United States Patent [19]
Bieling

[11] Patent Number: 5,460,600
[45] Date of Patent: Oct. 24, 1995

[54] UNIVERSAL FOOT SPLINT

[75] Inventor: Ross Bieling, Pinellas Park, Fla.

[73] Assignee: Select Medical Products, Pinellas Park, Fla.

[21] Appl. No.: 217,609

[22] Filed: Mar. 24, 1994

[51] Int. Cl.$^6$ .................................................. A61F 5/00
[52] U.S. Cl. .............................. 602/27; 128/882; 36/97
[58] Field of Search ...................... 602/5, 10, 11, 602/12, 14, 23, 27–29; 128/882; 36/97, 110, 103, 135, 89

[56] References Cited

U.S. PATENT DOCUMENTS

| Re. 33,762 | 12/1991 | Lonardo . | |
|---|---|---|---|
| 433,227 | 7/1890 | Beacock . | |
| 839,223 | 12/1906 | Stevens . | |
| 1,656,322 | 1/1928 | Fischer . | |
| 2,700,832 | 2/1955 | Slovinski | 36/97 X |
| 2,847,991 | 8/1958 | Andrews . | |
| 2,911,657 | 11/1959 | Streeter, III . | |
| 3,086,522 | 4/1963 | Frohmader . | |
| 3,345,654 | 10/1967 | Noble . | |
| 3,548,820 | 12/1970 | Bergen | 602/5 |
| 3,584,622 | 6/1971 | Domenico . | |
| 3,606,884 | 9/1971 | Peter . | |
| 3,618,946 | 11/1971 | Lee . | |
| 3,698,389 | 10/1972 | Guedel . | |
| 3,976,059 | 8/1976 | Lonardo . | |
| 4,178,925 | 12/1979 | Hirt | 36/97 X |
| 5,020,523 | 6/1991 | Bodine | 602/27 |
| 5,088,479 | 2/1992 | Detoro | 602/27 |
| 5,151,081 | 9/1992 | Williams | 602/27 |
| 5,154,695 | 10/1992 | Farris et al. | 602/27 |
| 5,224,925 | 7/1993 | Varn | 602/27 X |
| 5,269,748 | 12/1993 | Lonardo . | |

FOREIGN PATENT DOCUMENTS

| 937846 | 1/1956 | Germany . |
|---|---|---|
| 346649 | 7/1960 | Germany . |

Primary Examiner—Linda C. M. Dvorak
Attorney, Agent, or Firm—Pettis & McDonald

[57] ABSTRACT

A foot splint comprising a frame member fastened to the foot of a patient the frame member having a calf portion, a resilient heel portion spaced apart from the patient's heel, and an arch portion to which a ball extension member is slideably and lockably secured.

7 Claims, 9 Drawing Sheets 5,460,600

UNIVERSAL FOOT SPLINT

BACKGROUND OF THE INVENTION

FIELD OF THE INVENTION

The present invention relates to a foot splint for restraint and support of a foot. The splint is used to hold the foot in position during therapy and while the patient is resting.

Although previous foot splints have successfully restrained the foot of a patient in position during therapy and while the patient is resting, existing foot splints suffer from a lack of functionality, comfort, and economy since they must be produced in several sizes and only rarely correspond to the actual size of a patient's foot.

SUMMARY OF THE INVENTION

A foot splint is disclosed for restraining a foot of a patient the foot splint having a frame member with a heel portion, a calf portion and arch portion, the heel portion being resilient and spaced apart from the patient's heel, the calf portion extending upward from the heel portion along the patient's leg, and the arch portion extending along the bottom of the patient's leg and forming means for slidably securing an extension member extending to the ball of the foot of the patient, the extension member being releaseably locked in place by means for locking, and the resulting assembly then being attached to the foot of a patient using means for fastening.

As a result of the novel incorporation of an extension member into the present invention, the universal foot splint herein described may be produced without variation for all foot sizes and offers greater comfort and safety to the patient as a result of the exact fit to the patient's foot made possible by the present invention.

The invention accordingly comprises an article of manufacture possessing the features, properties, and relation of elements which will be exemplified in the article of manufacture hereinafter described and the scope of the invention will be indicated in the claims.

BRIEF DESCRIPTION OF THE DRAWINGS

For a full understanding of the nature and objects of the invention, reference should be had to the following detailed description taken in connection with the accompanying drawings in which.

Similar reference characters refer to similar parts throughout the several views of the drawings.

DETAILED DESCRIPTION

Figure 1:
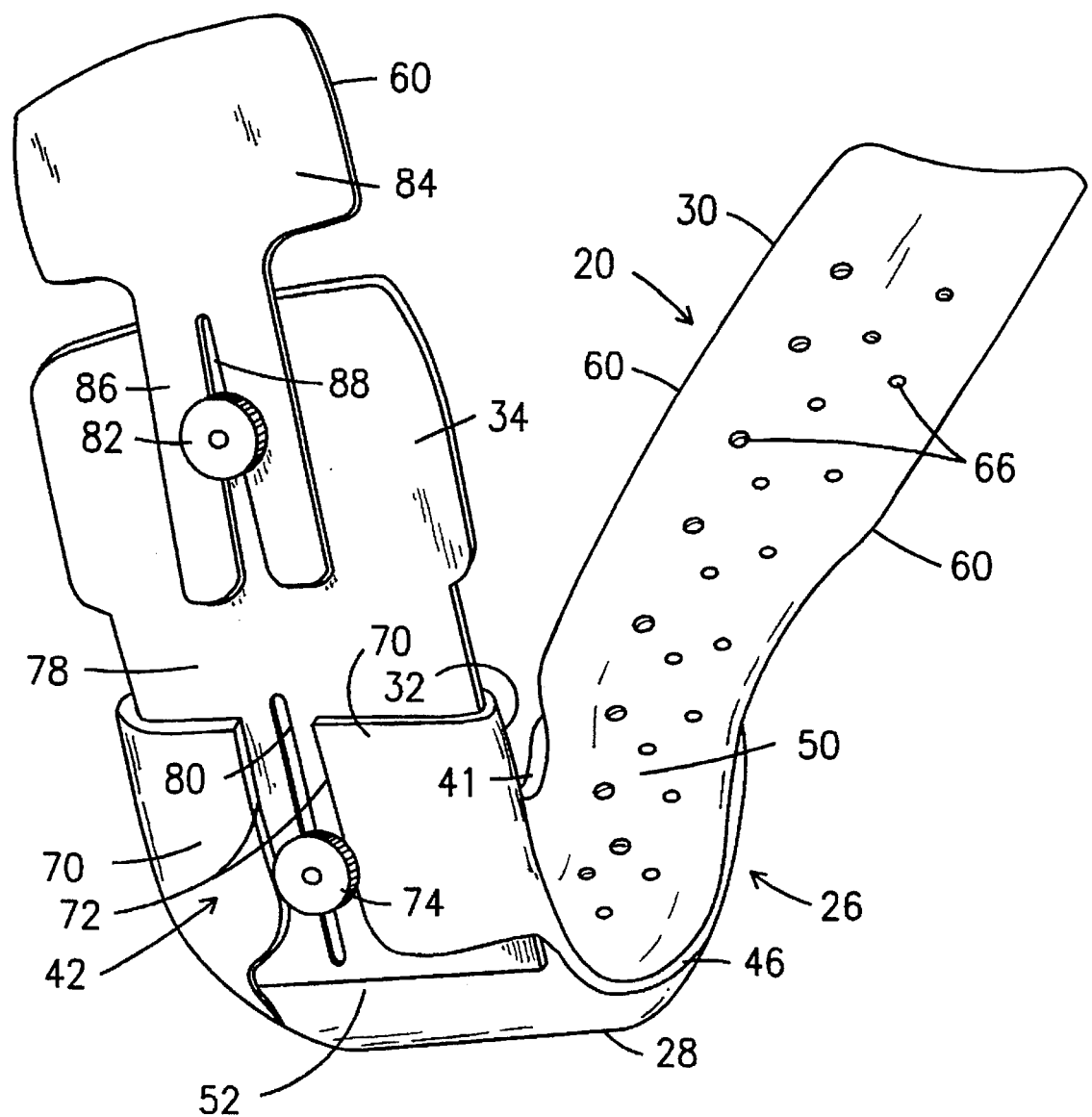
FIG. 1 is a perspective view of a universal foot splint according to the present invention.
Figure 3:
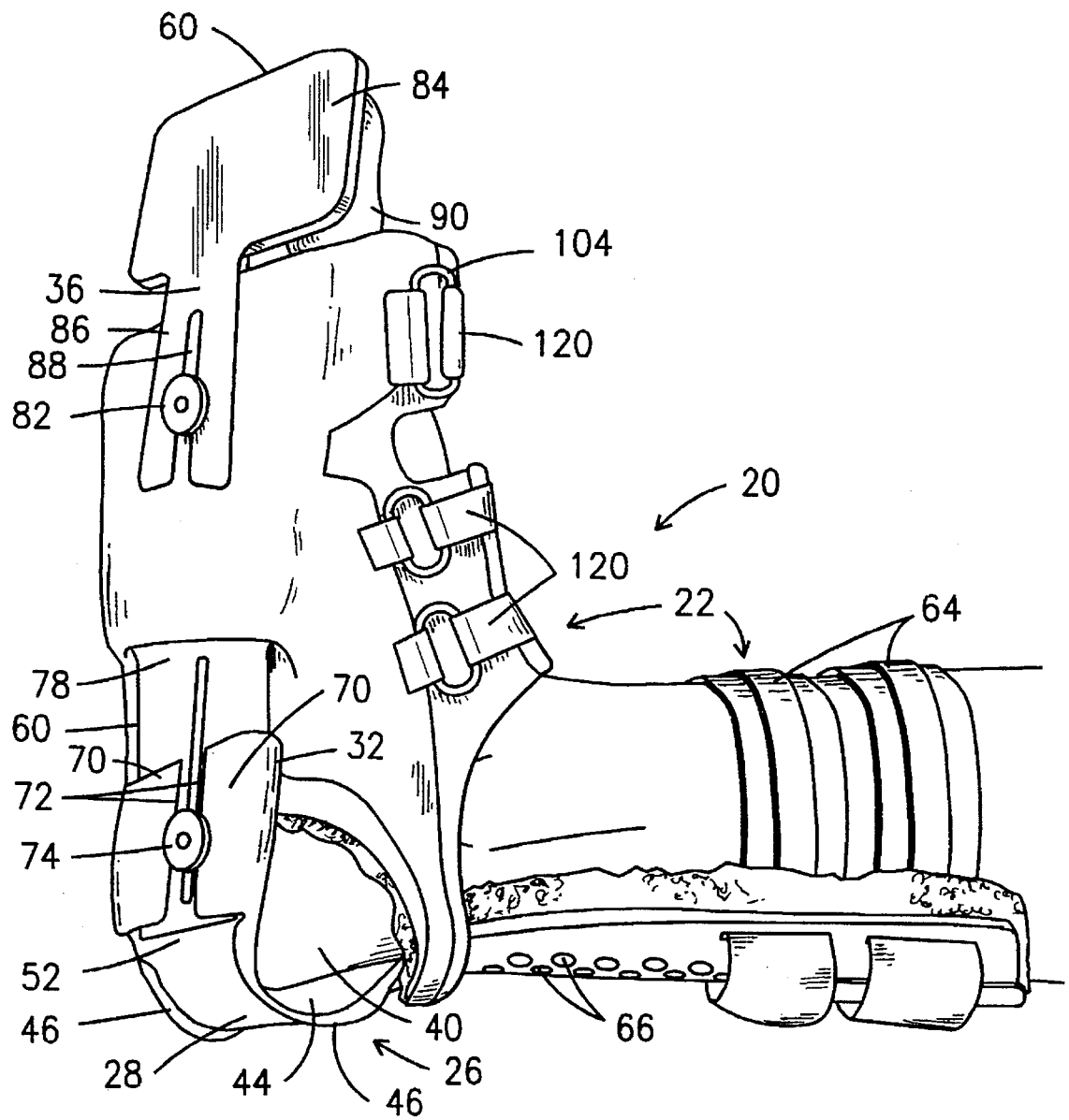
FIG. 3 is a perspective view of a universal foot splint according to the present invention, mounted to a foot by means for fastening.

In FIG. 1 a perspective view of the present invention is presented. In FIG. 3 a perspective view of the present invention including means for fastening, generally indicated as 22, and the foot, generally indicated as 24, of a patient is presented. For convenience and clarity, description of the present invention is divided into the following parts: a frame member, generally indicated as 26, made up of a heel portion 28, a calf portion 30, and an arch portion 32; a ball extension member 34; a toe extension member 36; means 74 and 82 for locking both the ball extension member 34 and the toe extension member 36; a rotation bar 38 (FIG. 7); and means 22 for fastening a foot 24 of a patient to the present invention (FIG. 3). These various parts will be described separately in the following sections.

Frame member

Figure 4:
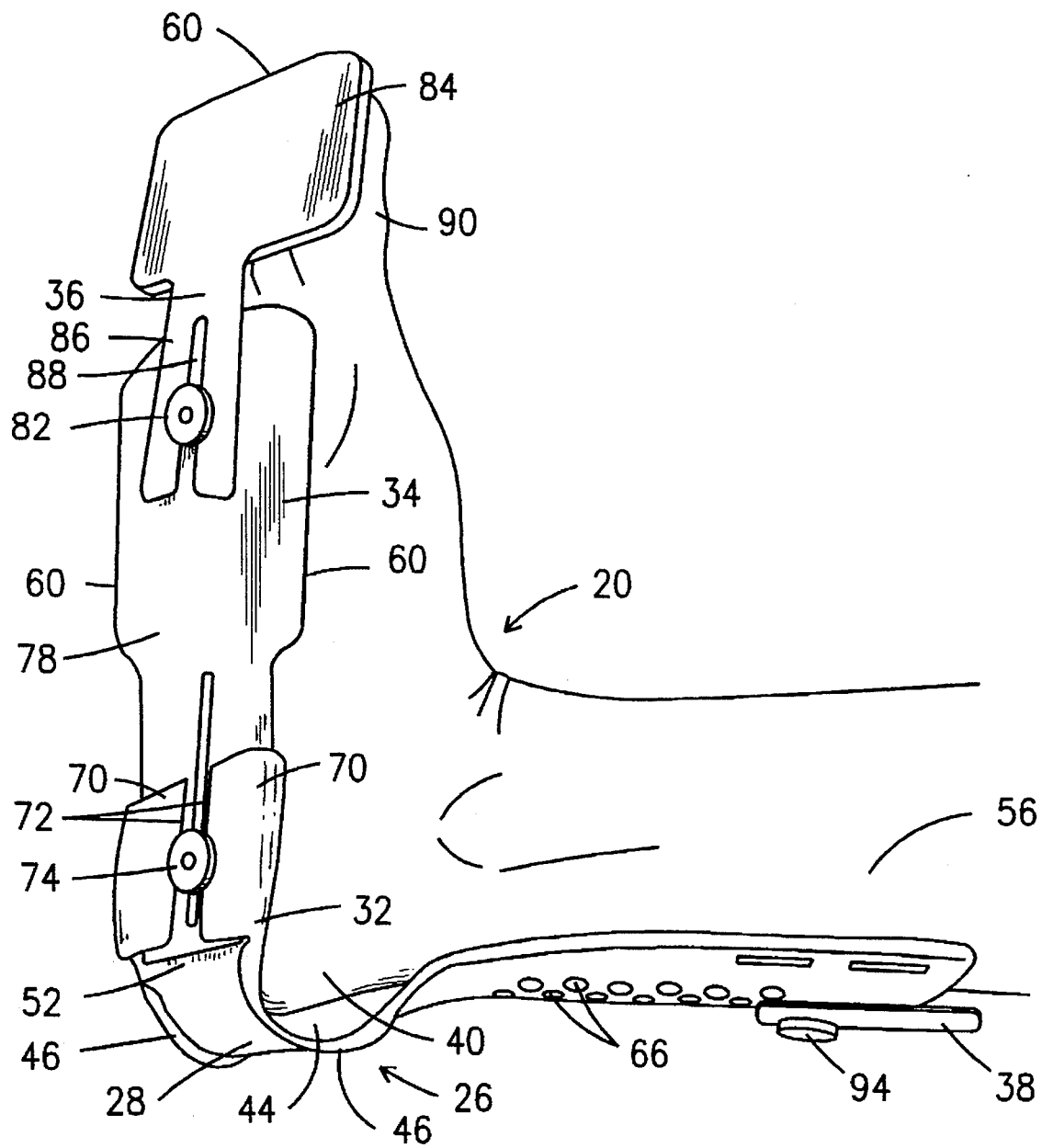
FIG. 4 is a perspective view of a universal foot splint according to the present invention, mounted to a foot, without means for fastening.
Figure 5:
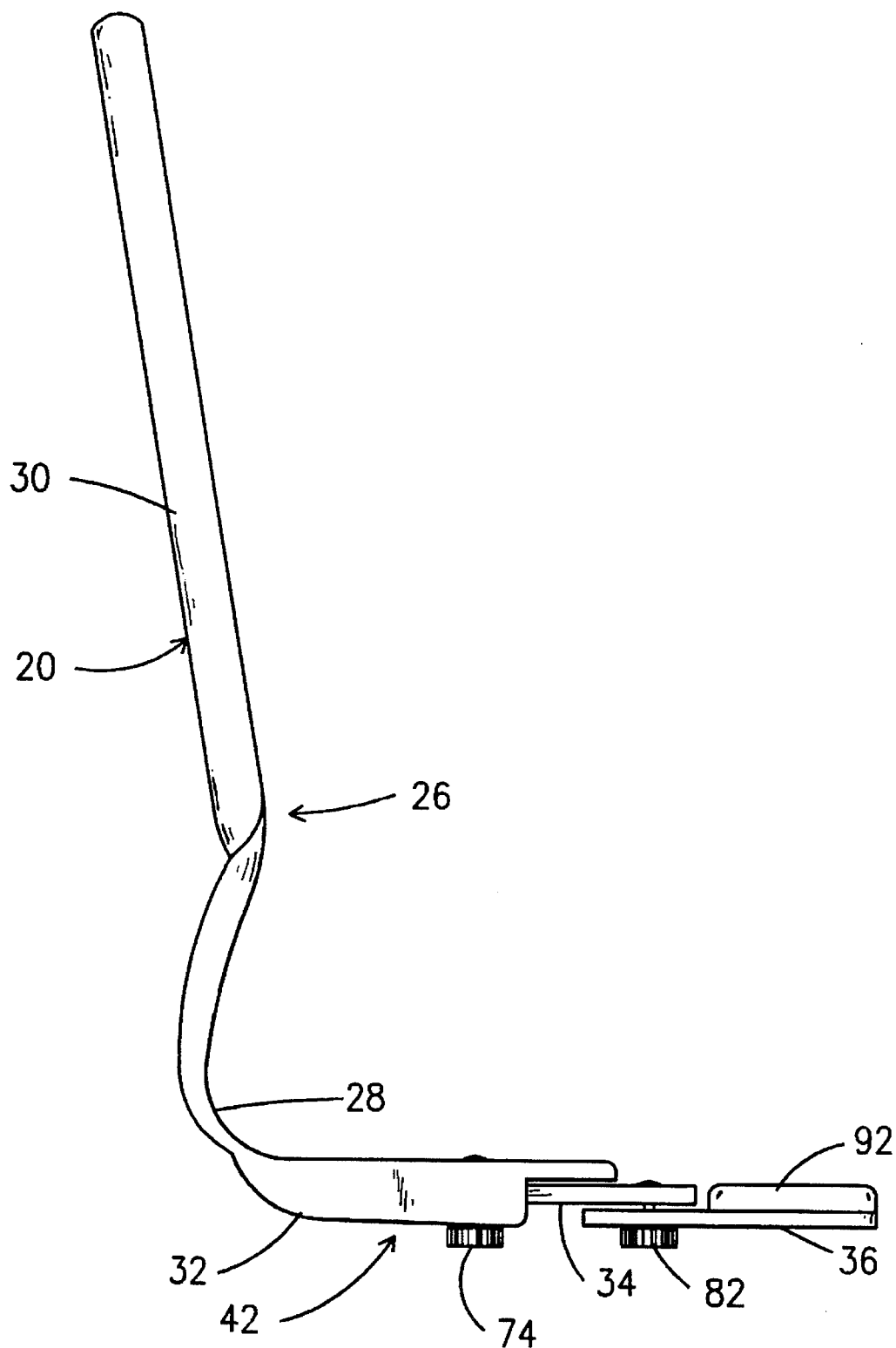
FIG. 5 is a side elevation of a universal foot splint.
Figure 6:
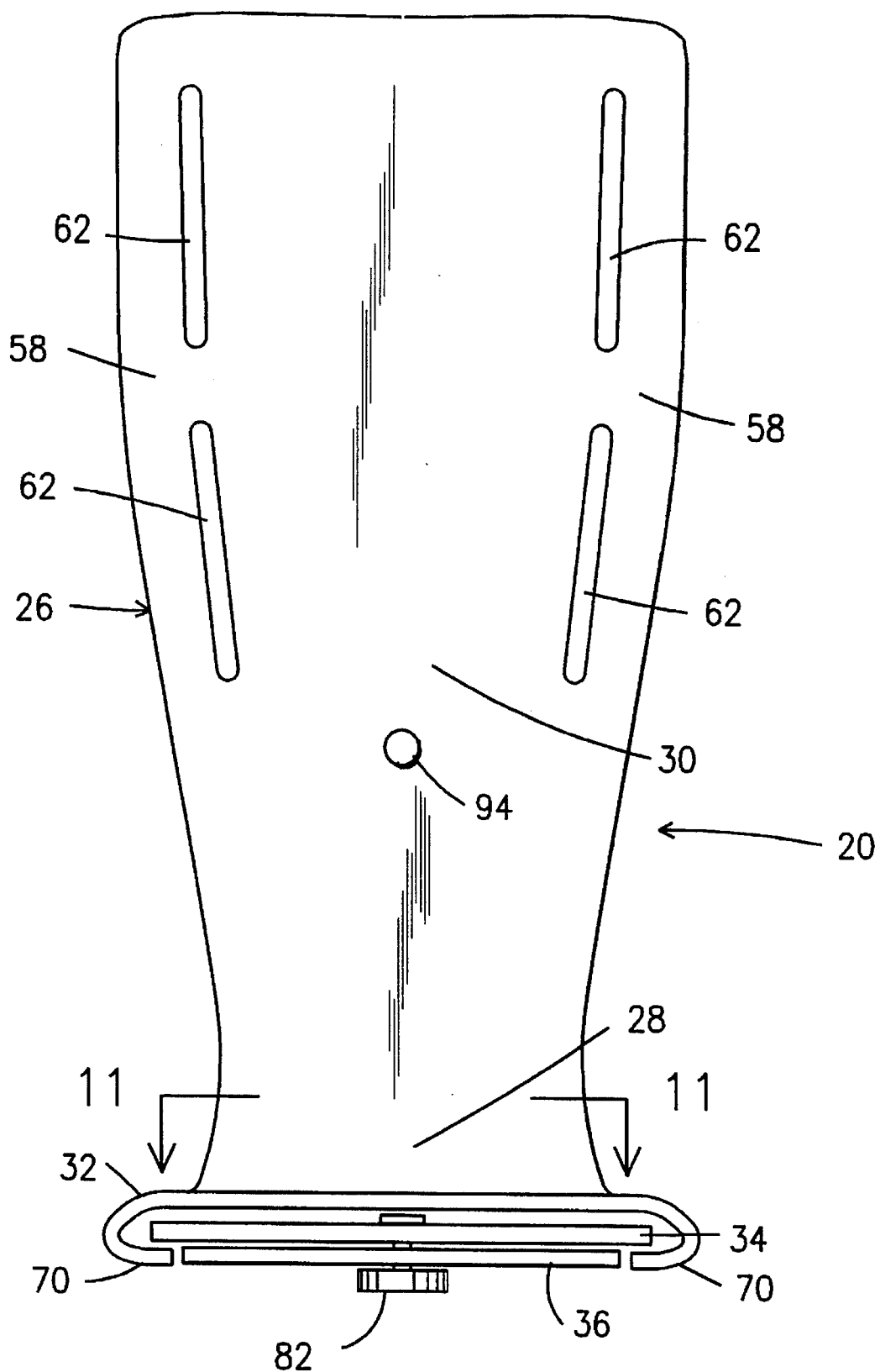
FIG. 6 is a front elevation of a universal foot splint.
Figure 7:
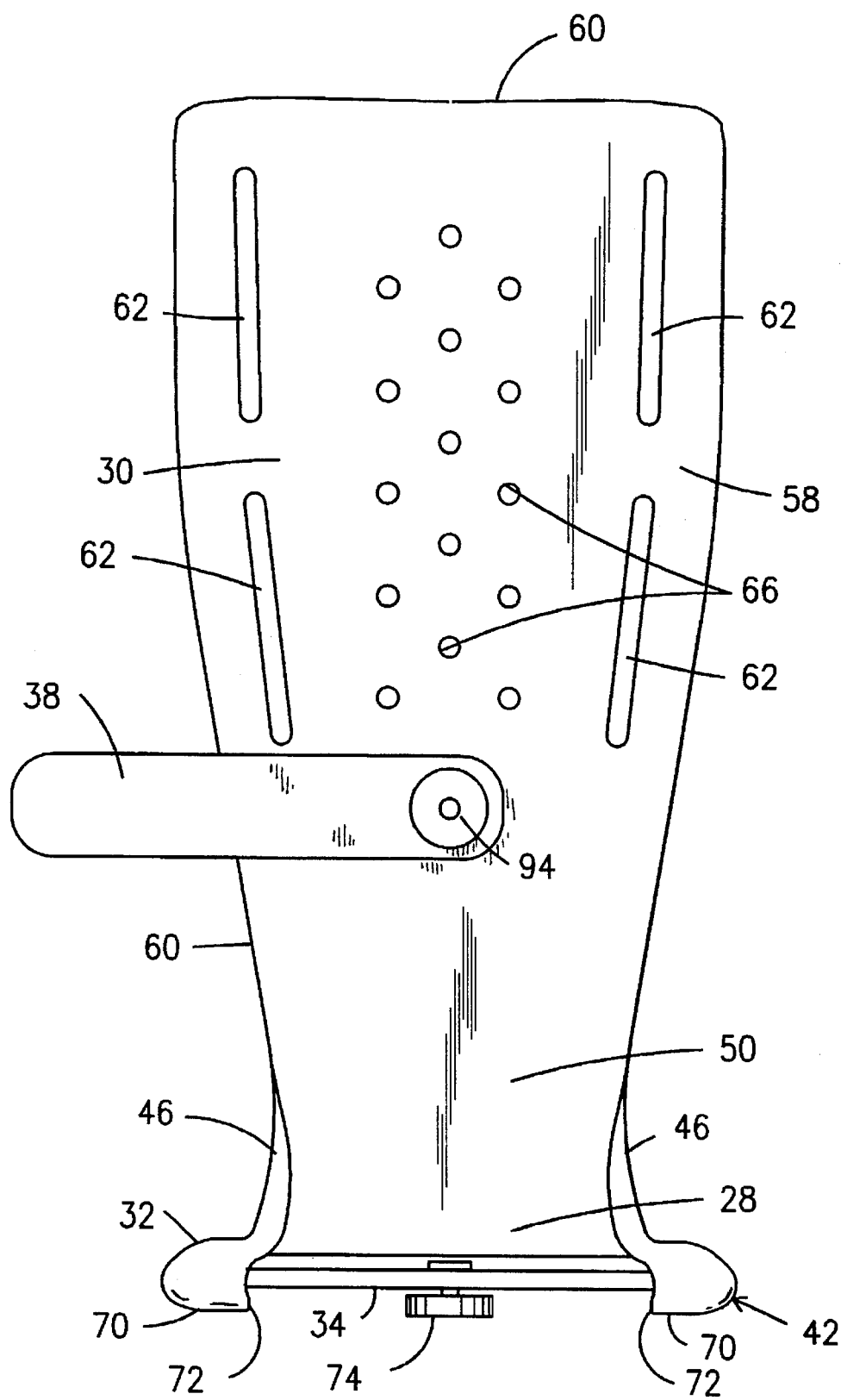
FIG. 7 is a rear elevation of a universal foot splint.
Figure 8:
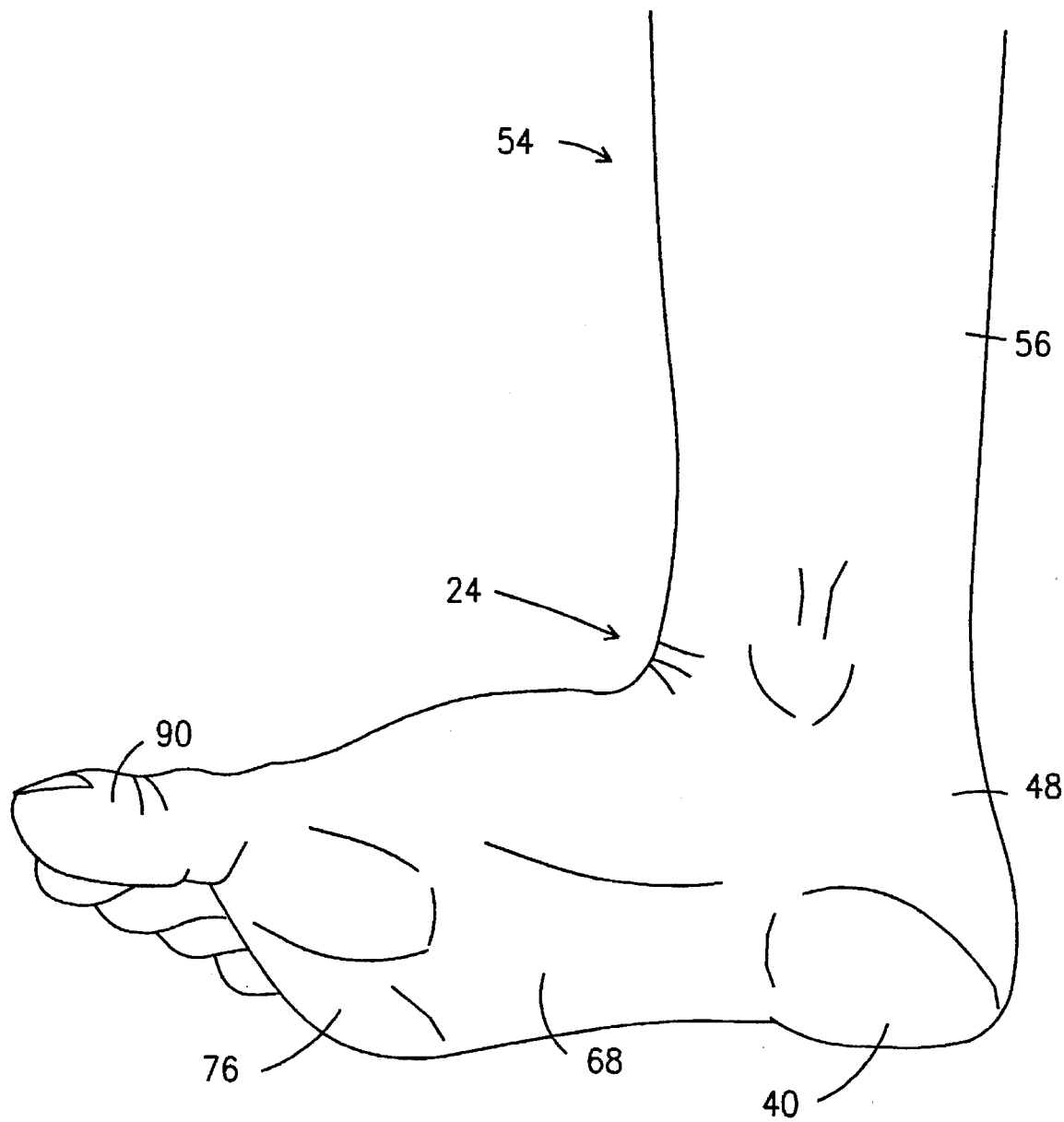
FIG. 8 is a perspective view of a foot.

The frame member 26 can be seen in a perspective view in FIG. 1 and is seen as it relates to the foot 24 of a patient in FIG. 4. In FIG. 5, the frame member 26 is shown in a side view, and FIGS. 6 and 7 present a front view and a rear view of the frame member 26. The frame member 26 is designed to support the foot 24 of a patient, although padding means may conveniently be placed between the foot 24 of a patient and the frame member 26 as seen in FIG. 3. The frame member 26 is an elongated broad strip of material, which may suitably be a resilient and shatter proof material, which is bent generally to conform to the curves of the patient's foot 24 . As seen in FIG. 4, the frame member 26 curves about the heel 40 of the patient's foot 24 and is straight or slightly curved above the heel portion 28 of the frame member 26, which corresponds to the heel 40 of the patient. Similarly, the portion of the splint, generally indicted as 20, extending from the heel portion 28 below the foot 24 of a patient, called the arch portion 32, is straight or slightly curved and includes means for slidably securing extension members, generally indicated as 42. Although the frame member 26, in a preferred embodiment, is formed of a single piece of material, this is not essential to its successful operation and construction. For clarity the frame member 26 will be described in three portions: The heel portion 28, the calf portion 30, and the arch portion 32.

Figure 11:
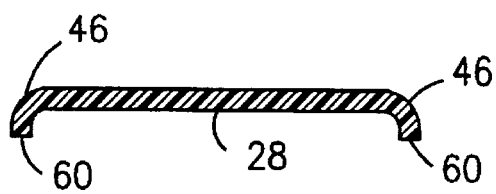
FIG. 11 is a cross sectional view of a heel portion taken along line 11—11 of FIG. 6.
Figure 12:
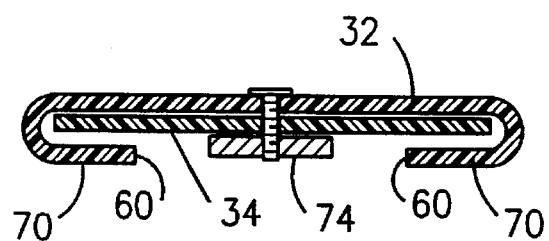
FIG. 12 is a cross sectional view of a universal foot splint through the arch portion taken along lines 12—12 of FIG. 2.

The heel portion 28 is formed of a resilient material which preferably is also elastic and shatter proof, so that when the heel portion 28 is deformed through stress placed upon it by the patient or due to other causes it will return substantially to its original shape. The heel portion 28 is curved as seen in FIGS. 4 and 5 around, and spaced apart from, the heel 40 of the patient so that an access space, generally indicated as 44, is maintained between the heel 40 of the patient and the heel portion 28 of the frame member 26. This access space 44 also permits visibility of the patient's heel 40. For improved resilience and tensile strength, a flange 46 may be created on both sides of the heel portion 28, which flange 46 may conveniently be turned away from the foot 24 of the patient as seen in FIG. 4. This preferred embodiment can be seen in FIG. 11 in cross section taken along line 11—11 of FIG. 6, where this preferred embodiment of the heel section 28 is shown as a substantially flat strip of resilient material with flanges 46 at its two edges.

These flanges 46 may conveniently be turned away from the patient's foot 24 to secure the added advantage of increasing the height of the foot 24 when the patient is resting their foot 24 and foot splint 20 on a surface, such as when the patient is lying on their back. This is even more beneficial in cases where the surface is soft and deformable, such as a soft mattress, in which case the heel portion 28 might press into the soft surface, obscuring view of the heel 40 of the patient.

At the upper end of the heel portion 28, where the heel portion 28 is closest to the back of the patient's heel 40 or patient's achilles tendon 48, the heel portion 28 continues into, engages, or attaches to the calf portion 30 of the frame member 26. For convenience, the part of the heel portion 28 which attaches into the calf portion 30 is called the calf extremity 50 of the heel portion 28. At the lower end, generally below the back of the heel 40 of the patient, the heel portion 28 forms an arch extremity 52 where it contacts, engages, attaches to, or continues into the arch portion 32 of the frame member 26.

As seen in FIGS. 5, 6, and 7, the calf portion 30 extends from the general area of the achilles tendon 48 of the foot 24 of the patient upward along the leg, generally indicated as 54, to provide support for the foot 24 of a patient and distribute any stresses upon the foot 24 along the leg 54. The calf portion 30 extends to some point along the calf 56 of the patient. In a preferred embodiment, the calf portion 30 is formed of a resilient, shatter proof material and may conveniently be curved and shaped to match the human leg 54. In a preferred embodiment, the lateral areas, generally indicated as 58, of the calf portion 30 may be curved toward the leg 54 of the patient, and the calf portion 30 may also conveniently curve back longitudinally so as to accommodate the curve from the achilles tendon 48 to the lower and upper calf 56 muscle. For the safety of patients, any exposed edges 60 of the materials of the present invention may conveniently be beveled or otherwise treated so that patients do not encounter a sharp edge.

As seen in FIG. 6, a front view of the foot splint 20 without means 22 for fastening attached, the calf portion 30 may widen as it extends upward from the heel portion 28 along the rear of the leg 54 of a patient.

The calf portion 30 may have two or more vertical slits 62. These vertical slits 62 are depicted in FIG. 6 and are generally vertical and are placed in the lateral areas 58 of the calf portion 30 for passing through straps 64 of the means 22 for fastening, thereby facilitating fastening the present invention to the foot 24 of a patient. As seen in FIG. 7 the longitudinal center line of the calf portion 30 of the frame member 26 may have ventilation openings 66 or holes 66 formed in or near it for ventilation and for the comfort of the patient's calf 56, leg 54, and foot 24 while wearing the present invention.

Figure 2:
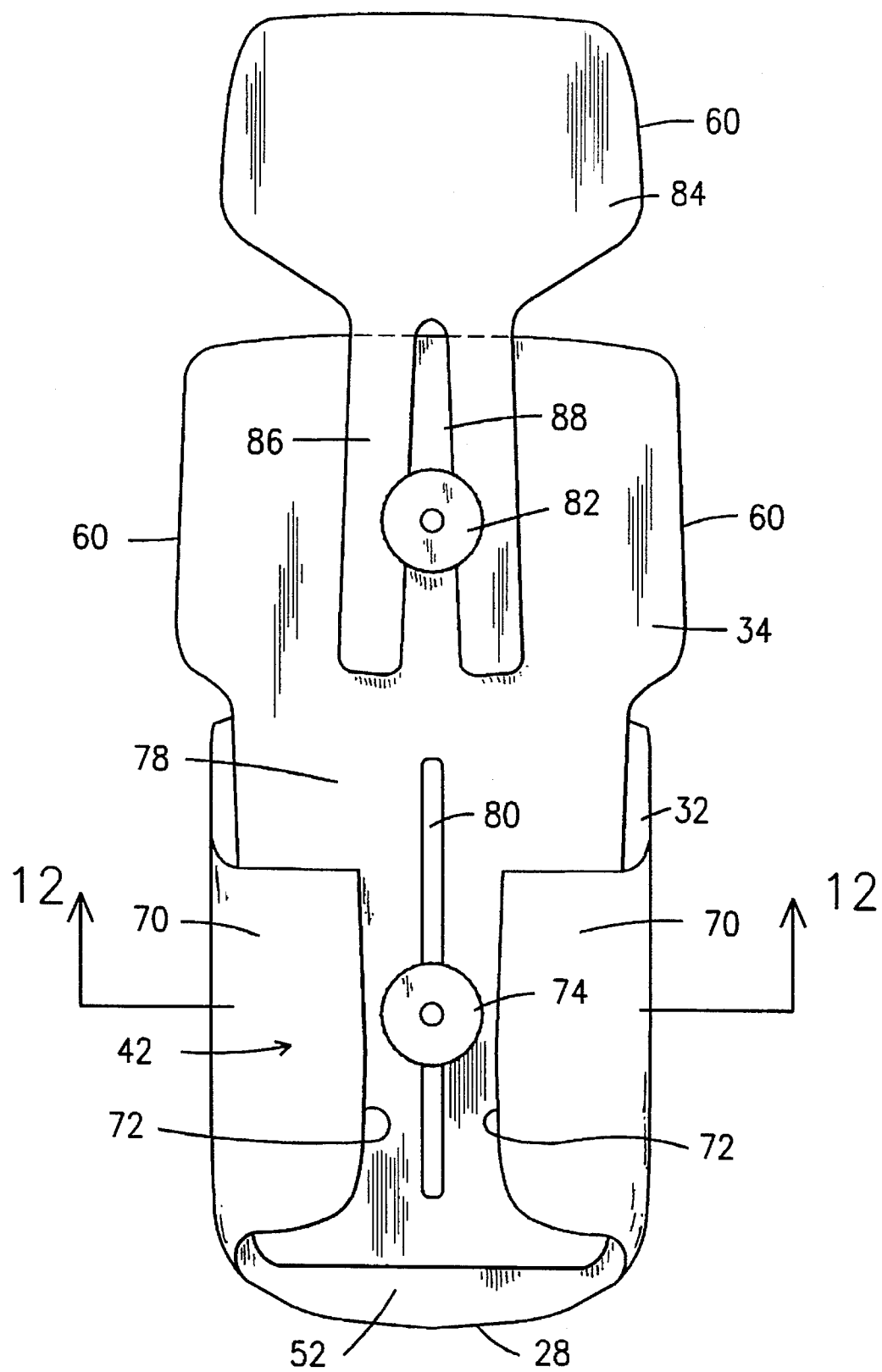
FIG. 2 is a bottom elevation of a universal foot splint according to the present invention.

The arch portion 32 extends from the arch extremity 52 of the heel portion 28 of the frame member 26 toward the arch 68 of the patient's foot 24 along the bottom of the patient's foot 24. In a preferred embodiment, the arch portion 32 may conveniently be made of a resilient shatter proof material. The arch portion 32 extends from a point corresponding to the patient's heel 40 to a point along the patient's arch 68, and may conveniently be generally the same width as the arch 68 of the patient's foot 24. The arch portion 32 provides means 42 for slidably securing extension members, which may be any securing means 42 known to the art, and may conveniently be two or more flaps 70, as shown in FIGS. 1, 2, 6 and 12, which fold below the arch portion 32 and extend toward each other substantially in a plane parallel to the plane defined by the arch portion 32. As seen in FIG. 2, the flaps 70 do not reach each other but leave a space between their extremities 72 for passage of the means 74 for locking. Between the arch portion 32 and the flaps 70 extending from the arch portion 32 a space is defined as seen in cross section in FIG. 12 taken along line 12—12 of FIG. 2 into which the ball extension member 34 can slide. The arrangement of flaps 70 limits the movement of the ball extension member 34 to sliding forward or backward relative to the foot 24 of the patient. The arch portion 32 may conveniently have a hole, opening, or other means for engaging the means 74 for locking.

Ball Extension Member

Figure 10:
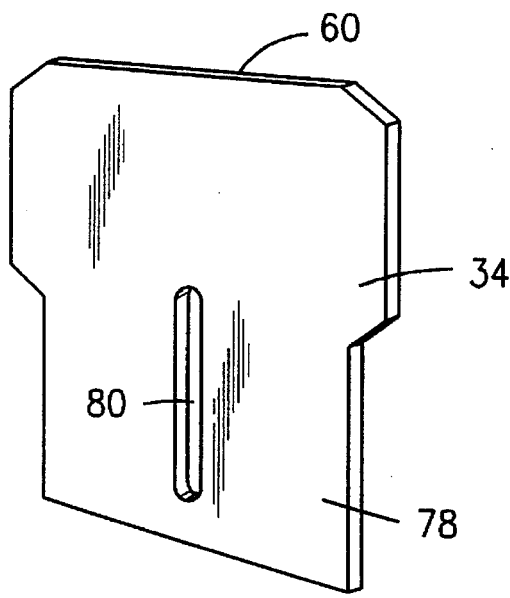
FIG. 10 is a perspective view of an alternate toe extension of a universal foot splint.

The portion of the foot splint 20 extending from the arch portion 32 of the frame member 26 to the general area of the ball 76 of the foot 24 of the patient is the ball extension member 34. The ball extension member 34 is a substantially flat, elongated strip of material as shown in FIGS. 1, 2, and 10. In a preferred embodiment, the ball extension member 34 may be made of a resilient, shatter proof material. A first portion 78 of the ball extension member 34 is designed to engage the means 42 for slidably securing extension members of the arch portion 32 of the frame member 26 and should therefore be no wider than the space defined by the flaps 70 of the arch portion 32 nor thicker than the space between the arch portion 32 and its flaps 70, so that the ball extension member 34 may slide in a forward and backward motion relative to the front and back of the foot 24 of the patient. The first portion 78 of the ball extension member 34 designed for this sliding motion may conveniently define a slot 80 disposed generally in the same direction as the forward and backward motion for passage of locking means 74. As shown in FIG. 10, the part of the ball extension member 34 which is not designed for engaging the means 42 for slideably engaging is not limited in width and may therefore be any shape and any width suitable to the function of this invention. A preferred embodiment is shown in FIGS. 1, 2, and 10, in which the ball extension member 34 is wider at its front end and is curved and beveled at its edges to reduce possible abrasion and injury to persons who come into contact with it. The ball extension member 34 may conveniently have an opening or other attachment location for means 82 for locking the toe extension member 36.

Toe Extension Member

In an optional embodiment a toe extension member 36 as depicted in FIGS. 1, 2, 3, 4, and 9 may be attached to the ball extension member 34. The toe extension member 36 is a substantially flat surface having a protruding portion 84 farthest from the arch portion 32 and a connection portion 86 along which a slot 88 is formed. The toe extension 36 is secured to the ball extension 34 by means 82 for locking. The means 82 for locking passes through the slot 88 in the connection portion 86 of the toe extension 36. The toe extension 36, when not locked in place by the means 82 for locking, is free to slide forward and backward (toward and away from the means for locking) and is also free to rotate about the means 82 for locking. When the means 82 for locking is in a locked position rather than a released position, the toe extension 36 is not free so to move.

The toe extension 36 provides the patient with a convenient place to rest the toes 90 during use of this device. For the comfort of a patient, a toe pad 92 may be mounted to the toe extension 36, so that the toes 90 of a patient will contact that pad 92. Depending on thickness of materials used in the means 22 for fastening the foot 24 of a patient to the foot splint 20, the toe extension 36 may be bent upward toward the toes 90 of the patient, so that the toes 90 of the patient may more easily contact the toe extension member 36 or the toe pad 92 on the toe extension member 36.

Figure 9:
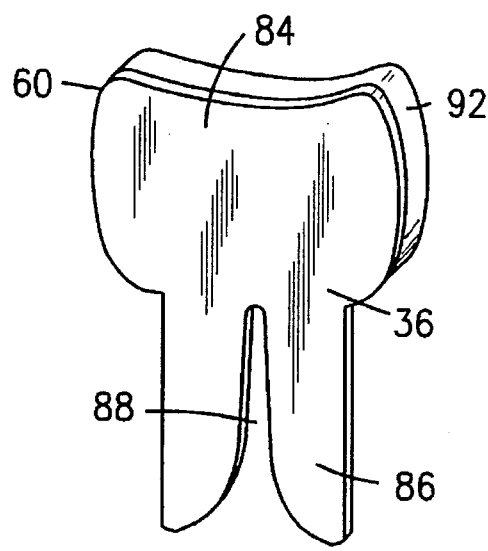
FIG. 9 is a perspective view of a toe extension of a universal foot splint.

FIG. 9 shows an optimal embodiment of the toe extension member 36 with a toe pad 92 mounted to it. The toe extension member 36 has a visible portion 84 to which the toe pad 92 is mounted and a connection portion 86 with a slot 88 for passage of the means 82 for locking.

Means for Locking

The means 74 for locking the ball extension member 34 to the arch portion 32 and the means 82 for locking the toe extension member 36 to the ball extension member 34 may both conveniently be a bolt driven through the arch portion 32 and the ball extension member 34, respectively, to which a nut is threaded and tightened so that pressure is then applied to the ball extension member 34 and the toe extension member 36 respectively, whereby the ball extension member 34 and the toe extension member 36 respectively are locked in position. Although means 74 and 82 for locking may suitably be bolt and nut arrangements, any other well known means for securing two surfaces to one another in a releasable fashion may be used, so long as a locked position and a released position are possible.

Rotation Bar

In an embodiment of the present invention, a rotation bar 38 is attached to the rear of the calf portion 30 of the frame member 26. The rotation bar 38 is secured to the calf portion 30 of the frame member 26 by locking means 94 or any other means 94 for securing, which may conveniently be a bolt and nut arrangement. The rotation bar 38 is capable of being swiveled to a position adjacent to and parallel to the calf portion 30 of the frame member 26, where it does not substantially add to the space required for storage of the foot splint 20, and does not get in the way of the patient using the foot splint 20 if the foot splint 20 is in use. In a rotated-out position such as the position shown in FIG. 7, when the patient is lying in bed or otherwise so positioned that the foot splint 20 calf portion 30 is in contact with a surface, the rotation bar 38, when extended, will prevent undesirable rotation of the foot 24 and undesirable strain upon the leg 54 of a patient, which rotation might otherwise damage the patient's recovery and/or health. Although the rotation bar 38 has been depicted as being shorter than the calf portion 30, any means for preventing rotation of the foot 24 and therefore of the leg 54 of a patient known to the art are suitable to the purposes of the present invention.

Means for Fastening the Foot of a Patient to the Present Invention

Referring to FIG. 3, a foot 24 of a patient is shown attached to the foot splint 20 of the present invention by use of means 22 for fastening the foot splint 20 to the foot 24. This preferred embodiment of means 22 for fastening also provides the function of padding the foot 24 of the patient against the foot splint 20, and thereby reducing pressure and damage, and resulting in a more comfortable use of the foot splint 20. The means 22 for fastening, or anklet 22, of this preferred embodiment of the present invention may suitably be made of a fleece material which straps to both the foot splint 20 and the foot 24 of the patient. The calf padding 96 rests upon the calf portion 30 of the frame member 26 and is held in place by at least one calf fastening strap 64. In an alternative embodiment, such as that depicted in FIG. 3, multiple calf straps 64 may be used. The calf padding 96 may conveniently be made of a fleece material, although any other padding which provides for suitable comfort of the patient may be used for this invention.

The foot portion, generally indicated as 98, of the anklet 22 may be a longitudinally cut tube of the same fleece material, and is held to the ball extension member 34 by a canvas overlay 100. The canvas overlay 100 forms a recess into which the ball extension 34 is fitted, and has a hole for passage of the means 82 for locking the toe extension 36 to the ball extension 34. From the canvas overlay 100, three straps 102 extend around the top of the foot 24 to the other side of the canvas overlay 100. These straps 102 may be any fastening means 102, but may conveniently be hook and eye fastening means passing through a buckle.

Although FIG. 3 does not depict an anklet 22 which completely covers the foot 24 of the patient it is not a requirement of the present invention that any portion of the foot 24 of the patient be visible. Any openings provided are therefore not necessary to the present invention, but rather depicted merely for the purposes of this preferred embodiment.

As a result of the incorporation of an extension member into the present invention, the universal foot splint herein described may be produced without variation for all foot sizes and offers greater comfort and safety to the patient as a result of the exact fit to the patient's foot made possible by the present invention's adjustability.

It will thus be seen that the objects set forth above and those made apparent from the preceding description are efficiently attained, and since certain changes may be made in the above article without departing from the scope of the invention, it is intended that all matter contained in the above description or shown in the accompanying drawings shall be interpreted as illustrative and not in limiting sense.

It is also to be understood that the following claims are intended to cover all of the generic and specific features herein described, and all statements of the scope of the invention which, as a matter of language may be said to fall there between.

Now that the invention has been described:

What is claimed is:

1. A foot splint for restraining a foot of a patient, the foot including a heel, a calf, an arch, a ball and toes extending from the ball, said foot splint comprising:

a frame member having a heel portion, a calf portion, and an arch portion, said heel portion being a resilient member having a calf extremity and an arch extremity, said heel portion being curved to extend about the patient's heel, such that said calf extremity is adapted to be proximal to the patient's calf, and such that said arch extremity is adapted to be proximal to the patient's arch, said heel portion being constructed to be spaced apart frown the heel, such that, when the patient's foot is restrained, the heel is substantially free from contact with said heel portion;

said calf portion attaching to said calf extremity and extending therefrom; and said arch portion attaching to said arch extremity and being adapted to extend therefrom along the patient's arch, said arch portion comprising means for slideably securing a ball extension member thereto;

a ball extension member engaging said means for slideably securing, said means for slideably securing comprising a plurality of flaps extending from said arch portion over said ball extension member, such that said ball extension member is slideably held proximal to said arch portion, said ball extension member being adapted to extend from said means for slideably securing to the patient's ball, and said ball extension member having an outer perimeter;

means for locking said ball extension member to said arch portion, such that said ball extension member is held in substantially one position, said means for locking said ball extension member having a released position and a locked position;

a toe extension member slideably engaging said ball extension member;

means for locking said toe extension member to said ball extension member, such that said toe extension member is held in substantially one position, said means for locking said toe extension member having a released position and a locked position; and means for fastening said foot splint to the patient's foot.

2. The foot splint of claim 1 wherein:

a line is defined passing substantially through the lateral center of said arch portion and said ball extension member; and said ball extension member comprises a slot through which said means for locking said ball extension member passes, such that said ball extension member may only travel parallel to said line when said means for locking said ball extension member is in said released position.

3. The foot splint of claim 2 wherein said toe extension member has a slot in it though which said means for locking said toe extension member passes, such that said toe extension member may only rotate about said means for locking said toe extension member or be moved toward or away from said means for locking said toe extension member, when said means for locking said toe extension member is in said released position.

4. The foot splint of claim 3, wherein said heel portion is flanged.

5. The foot splint of claim 4, wherein said calf portion is made of a resilient material, and said arch portion is made of a resilient material.

6. The foot splint of claim 5, wherein said frame member has a plurality of ventilation openings formed therethrough, said ventilation openings being spaced apart from each other.

7. The foot splint of claim 6, further comprising a toe pad mounted to said toe extension, such that, when the patient's foot is restrained, the toes will contact said pad.

\* \* \* \* \*

UNITED STATES PATENT AND TRADEMARK OFFICE
CERTIFICATE OF CORRECTION

PATENT NO.  : 5,460,600
DATED       : October 24, 1995
INVENTOR(S) : Ross Bieling It is certified that error appears in the above-indentified patent and that said Letters Patent is hereby corrected as shown below:

In the Claims:

Claim 1, column 6, line 51, delete "frown" and insert therefor --from--.

Signed and Sealed this

Thirtieth Day of April, 1996

Attest:

BRUCE LEHMAN

Attesting Officer

Commissioner of Patents and Trademarks